(12) United States Patent
Mains, Jr.

(10) Patent No.: US 10,772,957 B2
(45) Date of Patent: *Sep. 15, 2020

(54) METHOD, APPARATUS AND SYSTEMS FOR TRACKING FREIGHT

(71) Applicant: CRC R&D, LLC, Kenner, LA (US)

(72) Inventor: Ronald H. Mains, Jr., Kenner, LA (US)

(73) Assignee: CRC R&D, LLC, Kenner, LA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/029,409

(22) Filed: Jul. 6, 2018

(65) Prior Publication Data

US 2018/0326056 A1 Nov. 15, 2018

Related U.S. Application Data

(63) Continuation of application No. 14/521,361, filed on Oct. 22, 2014, now Pat. No. 10,019,878.

(Continued)

(51) Int. Cl.
*A61K 39/395* (2006.01)
*H04W 4/029* (2018.01)
(Continued)

(52) U.S. Cl.
CPC .... *A61K 39/3955* (2013.01); *C07K 14/70578* (2013.01); *C07K 16/2875* (2013.01); *G06Q 10/08* (2013.01); *G06Q 10/0833* (2013.01); *G08B 13/2434* (2013.01); *G08B 13/2462* (2013.01); *H04W 4/029* (2018.02);
(Continued)

(58) Field of Classification Search
CPC combination set(s) only.
See application file for complete search history.

(56) References Cited

U.S. PATENT DOCUMENTS 5,712,789 A * 1/1998 Radican ................. G06Q 10/08
700/226
6,556,138 B1 * 4/2003 Sliva ..................... B65F 1/1484
340/545.6

(Continued)

FOREIGN PATENT DOCUMENTS

WO 2006084255 8/2006

OTHER PUBLICATIONS

"Savings accrue from on-line from truck screening" https://www.itsinternational.com/sections/cost-benefit-analysis/features/savings-accrue-from-on-line-from-truck-screening/, last accessed on Jan. 7, 2020.

*Primary Examiner* — Travis R Hunnings
(74) *Attorney, Agent, or Firm* — Jason P. Mueller; FisherBroyles, LLP (57) ABSTRACT

Methods, apparatus, and systems are provided for tracking freight. Embodiments include a tracking device for a trailer containing a load. The tracking device includes a support member, a connector, a housing and a GPS tracker configured to track the location of the load. The connector securely attaches to a container on the trailer and attaches to a seal such that the container cannot be opened without breaking the seal. The support member stabilizes the housing and protects the tracking device during transit of the load. A tracking system may implement to monitor, gather information and report on the tracking device and the load.

25 Claims, 11 Drawing Sheets

Related U.S. Application Data (60) Provisional application No. 62/064,331, filed on Oct. 15, 2014.

(51) Int. Cl.
*G06Q 10/08* (2012.01)
*G08B 13/24* (2006.01)
*C07K 14/705* (2006.01)
*C07K 16/28* (2006.01)
*A61K 38/00* (2006.01)
*A61K 39/00* (2006.01)

(52) U.S. Cl.
CPC ........ *A61K 38/00* (2013.01); *A61K 2039/505* (2013.01); *C07K 2317/52* (2013.01); *C07K 2319/30* (2013.01)

(56) References Cited

U.S. PATENT DOCUMENTS

| | | | | |
|---|---|---|---|---|
| 7,312,702 B1* | 12/2007 | Willms | ........... | G06Q 10/08 340/540 |
| 8,219,503 B2* | 7/2012 | Takahashi | ........... | G06Q 10/063 705/330 |
| 8,279,067 B2* | 10/2012 | Berger | ........... | G06Q 10/08 340/572.1 |
| 10,019,878 B2* | 7/2018 | Mains, Jr. | ........... | G08B 13/2434 |
| 2003/0063000 A1* | 4/2003 | Grimm | ........... | G01S 5/0027 340/568.7 |
| 2004/0155778 A1* | 8/2004 | Shek | ........... | G06K 7/0008 340/572.1 |
| 2005/0071247 A1* | 3/2005 | Kelley | ........... | G06Q 10/08 705/330 |
| 2005/0116833 A1* | 6/2005 | Miller | ........... | G01M 5/0008 340/690 |
| 2005/0231365 A1* | 10/2005 | Tester | ........... | G06K 19/07798 340/568.1 |
| 2006/0109106 A1* | 5/2006 | Braun | ........... | G06Q 10/08 340/539.13 |
| 2009/0265223 A1* | 10/2009 | Takahashi | ........... | G06Q 10/063 705/333 |
| 2009/0322510 A1* | 12/2009 | Berger | ........... | G06Q 10/08 340/539.1 |
| 2011/0128143 A1* | 6/2011 | Daniel | ........... | G06Q 10/08 340/539.1 |
| 2011/0133888 A1* | 6/2011 | Stevens | ........... | G06Q 50/28 340/8.1 |
| 2011/0133932 A1* | 6/2011 | Tan | ........... | G09F 3/0317 340/568.1 |
| 2013/0016636 A1 | 1/2013 | Berger et al. | | |
| 2014/0067313 A1* | 3/2014 | Breed | ........... | G06K 9/00771 702/141 |
| 2014/0218218 A1* | 8/2014 | Lloreda | ........... | E05B 39/005 340/989 |
| 2015/0081582 A1 | 3/2015 | Mains, Jr. | | |

\* cited by examiner

FastTrack

- Dashboard
- Search
- Reports

Home / Reports

Customer A

| Customer | BOL | Origin | Destination | Appointment Time | ETA | Status |
|---|---|---|---|---|---|---|
| Customer A | 10000 | Geismar, LA | Decatur, TX | 9/25/2014 3:42:49 PM | 9/26/2014 6:19:40 PM | Late |
| Customer A | 10001 | Geismar, LA | Decatur, TX | 9/25/2014 11:48:21 AM | 9/26/2014 6:32:00 AM | Late |
| Customer A | 10002 | Geismar, LA | Decatur, TX | 9/25/2014 7:00:02 PM | 9/26/2014 11:47:44 AM | On Time |
| Customer A | 10003 | Geismar, LA | Decatur, TX | 9/27/2014 4:21:16 AM | 9/26/2014 8:31:33 AM | Late |
| Customer A | 10004 | Geismar, LA | Decatur, TX | 9/27/2014 4:07:07 PM | 9/26/2014 8:55:19 AM | On Time |
| Customer A | 10005 | Geismar, LA | Decatur, TX | 9/26/2014 8:36:10 AM | 9/26/2014 3:17:32 PM | On Time |
| Customer A | 10006 | Geismar, LA | Decatur, TX | 9/26/2014 5:49:16 AM | 9/26/2014 9:55:38 PM | Late |
| Customer A | 10007 | Geismar, LA | Decatur, TX | 9/25/2014 5:48:51 PM | 9/26/2014 10:03:47 AM | Late |
| Customer A | 10008 | Geismar, LA | Decatur, TX | 9/25/2014 2:03:22 PM | 9/26/2014 2:43:25 PM | Late |
| Customer A | 10009 | Geismar, LA | Decatur, TX | 9/27/2014 12:02:16 AM | 9/26/2014 8:42:02 PM | On Time |

Showing 1 to 10 of 10 entries

Previous 1 Next

Customer B

FIG. 12

FIG. 13

METHOD, APPARATUS AND SYSTEMS FOR TRACKING FREIGHT

CROSS-REFERENCE TO RELATED APPLICATIONS

This application is a continuation of U.S. patent application Ser. No. 14/521,361, filed on Oct. 22, 2014, which claims the benefit of U.S. Provisional Patent Application No. 62/064,331 filed on Oct. 15, 2014, the entire contents of each of which are incorporated herein by reference.

FIELD

The present invention relates to methods, apparatuses, and systems for the tracking of freight, and in particular though non-limiting embodiments, to methods, apparatus, and systems for tracking sealed trucks and containers by global position systems ("GPS") via wireless communication.

BACKGROUND

GPS systems and mobile tracking applications are used to track freight in the transportation industry. Many existing systems, however, are prone to error for various reasons. Common problems include: durability and operability under adverse conditions; functionality in directly tracking a container containing cargo; and security. Regarding durability and operability, existing systems have typically not included housings capable of withstanding the swaying, bumps, wind, weather and other adverse conditions often encountered during truck transport. Regarding functionality, existing systems may provide incorrect information as to location of the actual load being transported because they are connected to the tractor and/or driver and are not connected to the actual container housing the cargo. Indeed, it is not uncommon for existing systems to be hardwired to freight hauling tractors and/or linked to a driver's cell phone. Regarding security, existing systems may be tampered with and are typically not integrated with existing security systems for the container housing the cargo.

SUMMARY

Embodiments of the present invention address the problems described above with respect to existing GPS receiver systems and mobile tracking applications that have been used to track freight in the transportation industry. Indeed, the present invention provides for new and improved methods, apparatuses and systems for tracking freight.

In an example embodiment of the present invention a system is provided that includes a removable tracking device; a seal; and a container. The tracking device is integrated with and/or securely attached to the seal and/or the container such that the container cannot be accessed without breaking the seal.

In another example embodiment of the present invention, a system for broker trucking is provided that includes at least one container including a load, a removable tracking device configured to continuously transmit a location of the container, the container sealed with a seal to prevent access to the load and tracking device without breaking the seal; a computer configured to continuously receive the location of the container from the respective removable tracking device; and a user interface configured to display the transmitted location of the at least one container as received by the computer to an administrator.

In yet another embodiment of the present invention, a method of broker trucking is provided that includes the following steps: obtaining a tracking device and a bill of lading for a load; loading a container, connected to a trailer, with the load; sealing the container such that neither the load, tracking device or bill of lading can be accessed without breaking the seal; monitoring the container while the load is in transit; breaking the sealed container upon the arrival at a place of load delivery; removing the load from the container; and returning the tracking device and the bill of lading to a depository. In yet another embodiment of the present invention, a tracking device for a trailer containing a load is provided that includes a support member, a connector, and a main body/housing enclosing a GPS tracker configured to track the location of the load. The connector is connected to the support member, the support member is connected to the main body and the GPS tracker is located within the main body. The connector securely attaches to a container on the trailer and attaches to a seal such that the container cannot be opened without breaking the seal. The support member stabilizes the housing and protects the tracking device during transit of the load.

DESCRIPTION

The present invention provides methods, apparatuses, and systems for tracking of freight, including methods, apparatuses, and systems for tracking sealed trucks and containers by GPS via wireless communication.

According to an example embodiment of the present invention, a truck pulls up to a warehouse. Personnel greet the driver and load a trailer with appropriate freight and provide a bill of lading to the driver. Closing the trailer and/or container loading door(s) the personnel lock the load with a tracking device such that the tracking device is secured to the door(s) and a seal. The tracking device cannot be removed, or the door(s) opened, without breaking the seal. With the trailer loaded, secured and ready to depart, personnel approach a local terminal notifying a tracking system that the load is ready to depart or has departed. The tracking system processes the notification and initiates freight load tracking. The tracking system gathers information during transit of the load and processes the information for use by administrators. The administrators may monitor the load, update arrival times, connection times, and customers as to the status of the load. Once the load arrives at its destination, personnel break the seal, unload the trailer or container, and update the tracking system accordingly. The destination warehouse then forwards the tracking device to an appropriate location.

In various embodiments, the tracking system includes a container/trailer and tracking device configured to securely and universally integrate with existing load seals. The tracking device houses electronic circuitry and microcontrollers (mainboard, accelerometer, GPS tracker, GSM communication, power supply, satellite communication, optional additional sensors—e.g. temperature, vibration, and seal) and interfaces with a tracking system that may be web based. The tracking device electronic circuit board/s collect/transmit acceleration and GPS data to the web application via GSM and/or satellite communication. The tracking device and/or tracking system provide an administrator with tracking data which may be utilized for various purposes, including administration, reporting, and searching. This data may be automatically or manually entered into an existing company Transportation Management System.

Figure 1:
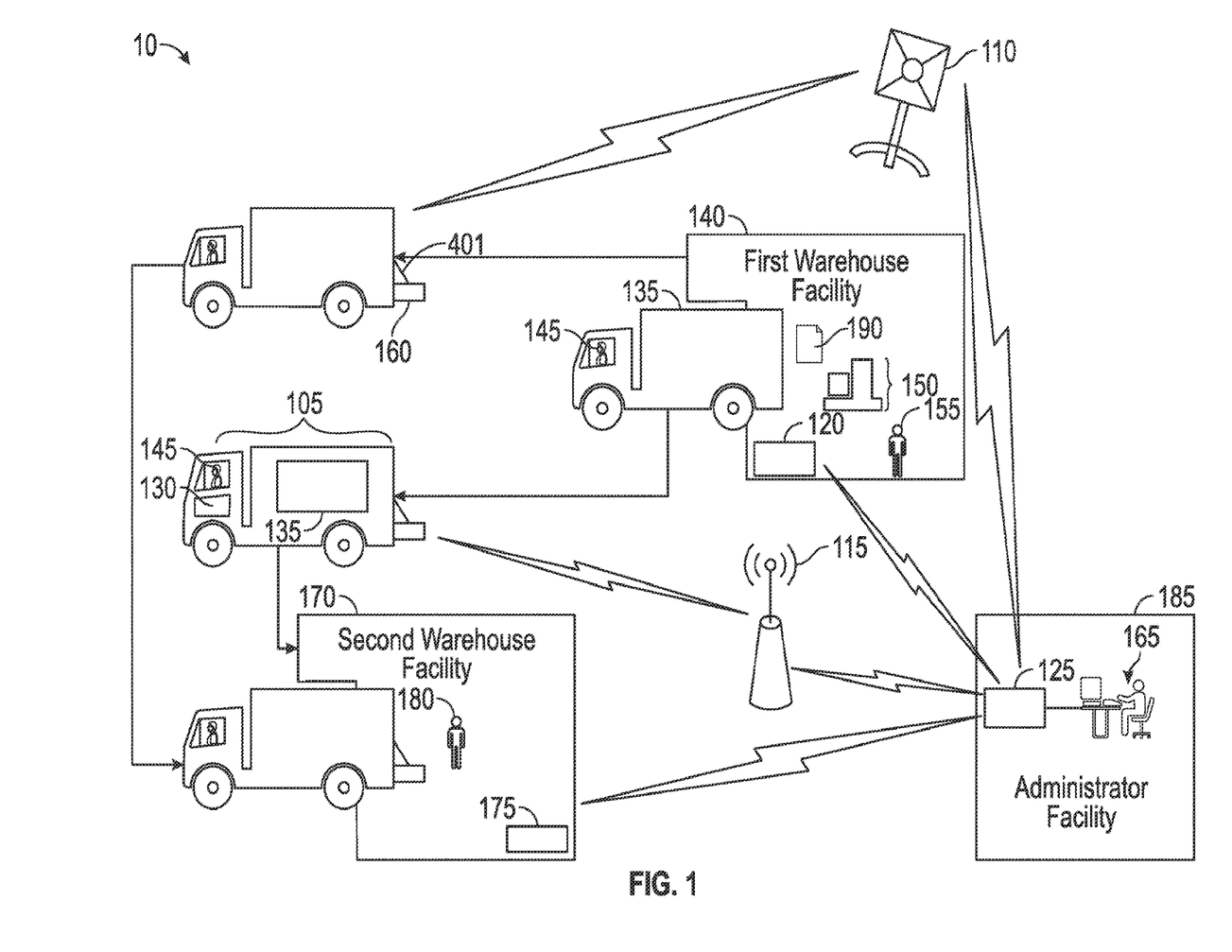
FIG. 1 is a schematic overview of a freight tracking system, according to an exemplary embodiment of the present invention.

FIG. 1 schematically depicts a tracking system (10) including warehouses (140, 170), a bill of lading (190), a container (135), bolt seal (401) and a tracking device (160). In various embodiments of the present invention the system may include greater or fewer components. At a first warehouse facility (140) a bill of lading (190) is given to driver (145) and load (150) is loaded into a trailer (135) (or a container located on the trailer) by warehouse personnel (155). The trailer/container and tracking device (160) are placed together and then a seal is used to secure the load. In one embodiment the trailer/container includes doors that are latched together with overlapping flanges that include a central hole. Tracking device (160) includes a connector that attaches to the overlapping flanges of the doors and includes an aperture that aligns with the central hole of the doors. The seal may be a bolt seal that passes through the hole in the door flanges and the aperture in tracking device (160). An end piece is then placed on the seal such that the doors, tracking device and seal are secured together. The doors cannot be opened and the tracking device (160) cannot be removed and/or tampered with without breaking the seal. Warehouse personnel (155) may then input into a tracking system that the load is ready to leave local terminal (125) and activate tracking. The trailer (135) departs the first warehouse and while in transit via GSM (115) and/or satellite (110) continuously informs the tracking system computer (125) of the trailer/containers (135) position. Once the trailer (135) arrives at a second warehouse facility (170), warehouse personnel (180) unload the load (150). After unloading, personnel update a terminal (175) deactivating tracking system tracking by the tracking system computer (125).

The system of the present disclosure may include a first (140), second (170), or further plurality of warehouse facilities. Furthermore, the warehouse facilities are not limited to enclosed truck freight logistic centers but may include docks, ships, or other facilities where efficient routing of cargo/freight is advantageous.

The bill of lading (190) of the present disclosure can take physical or digital forms documenting the cargo while giving title to a specified party (e.g. delivery warehouse operator). The bill of lading can be stored at various warehouse facilities and/or digitally within the tracking device itself.

The trailer/container of the present disclosure can vary based on different embodiments. In some instances a container is attached to a trailer and pulled by a tractor. In other instances the container is part of the trailer and is pulled by a tractor. In other instances the tractor, trailer and container are one unit. In other instances the container may be a shipping container, smaller container or the like that may be loaded on ships or other forms of transport such as cargo planes and helicopters.

Figure 2:
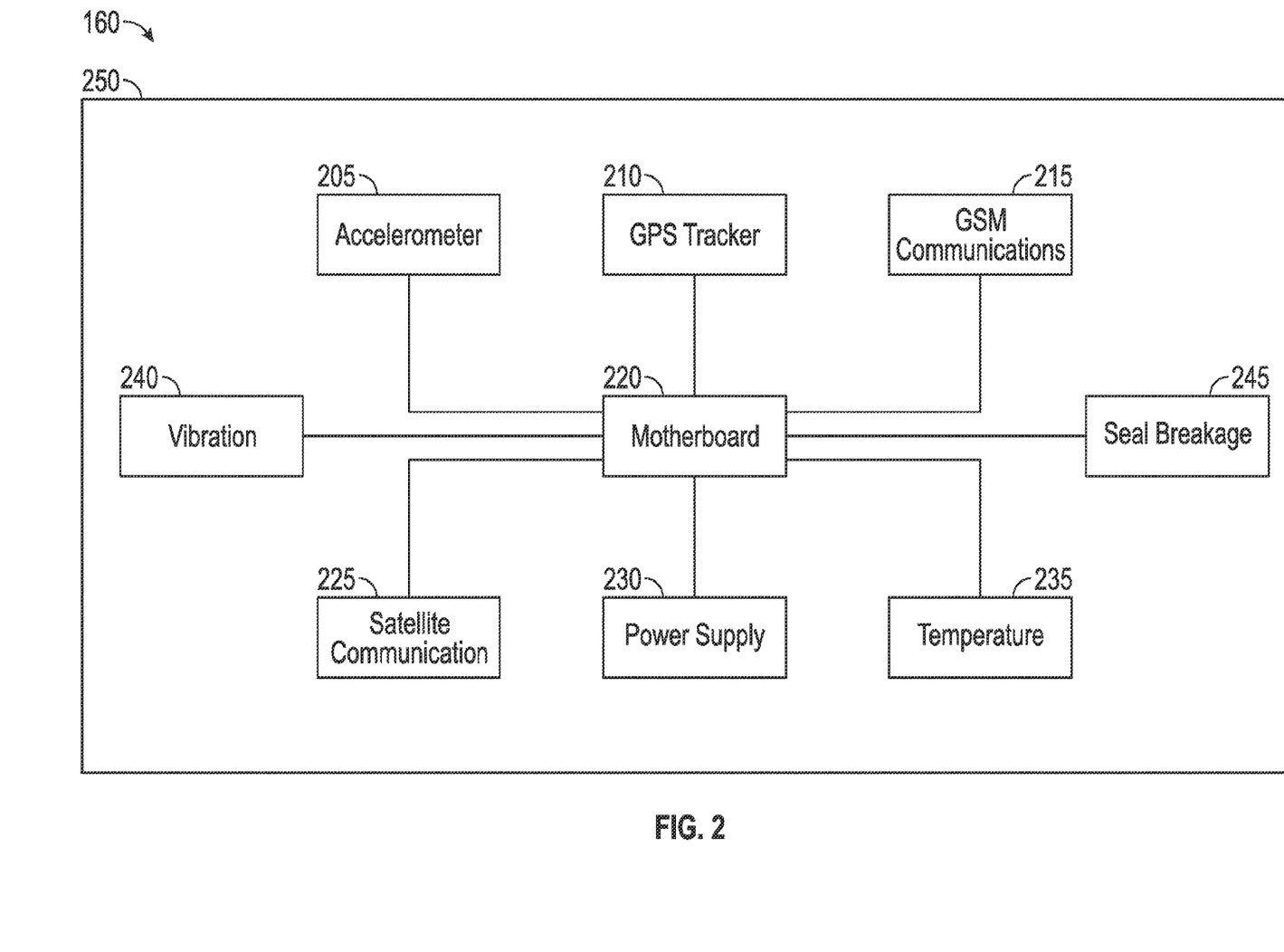
FIG. 2 is a schematic of a tracking device, according to an exemplary embodiment of the present invention.

In various embodiments of the system the tracking device (160) can take many forms. FIG. 2 shows a schematic of a tracking device (160) according to an exemplary embodiment of the present invention. As depicted, the tracking device (160) includes accelerometer (205), GPS tracker (210), GSM communications (215), satellite communications (225), power supply (230) and temperature (235), vibration (240), and seal breakage (245) sensors operably connected to a mainboard, and located within a housing (250). In various embodiments the tracking device (160) may include greater or fewer components and may be configured to weigh less than ten pounds.

The accelerometer (205) can provide local acceleration information to the system. The accelerometer (205) can indicate whether the velocity of the tracking device (160) is increasing or decreasing. For example, in a high wind environment, the device (160) may sway causing damage to the components and/or container cargo. The accelerometer (205) may log and monitor these local stresses. The accelerometer (205) can be, as pictured in FIG. 3, a LIS344AL (305). A LIS344AL (305) is a low-power three axis linear accelerometer that includes a sensing element and analog IC interface.

For monitoring the tracking device (160) position, a GPS tracker (210) can be included in an embodiment of the present invention. The GPS tracker (210) can be connected to a variety of systems including but not limited to the Global Positioning System ("GPS'), the Global Navigation Satellite System ("GLONASS"), and/or the BeiDou Navigation Satellite System. The GPS tracker (210) has the ability to receive information concerning the latitudinal and longitudinal position of the tracking device (160). The GPS tracker may also be configured to translate received latitudinal and longitudinal information into velocity and acceleration. The GPS tracker (210) can comprise a Ultimate GPS Module (310) as pictured in FIG. 3 and built around the MTK3339 chipset.

Figure 3:
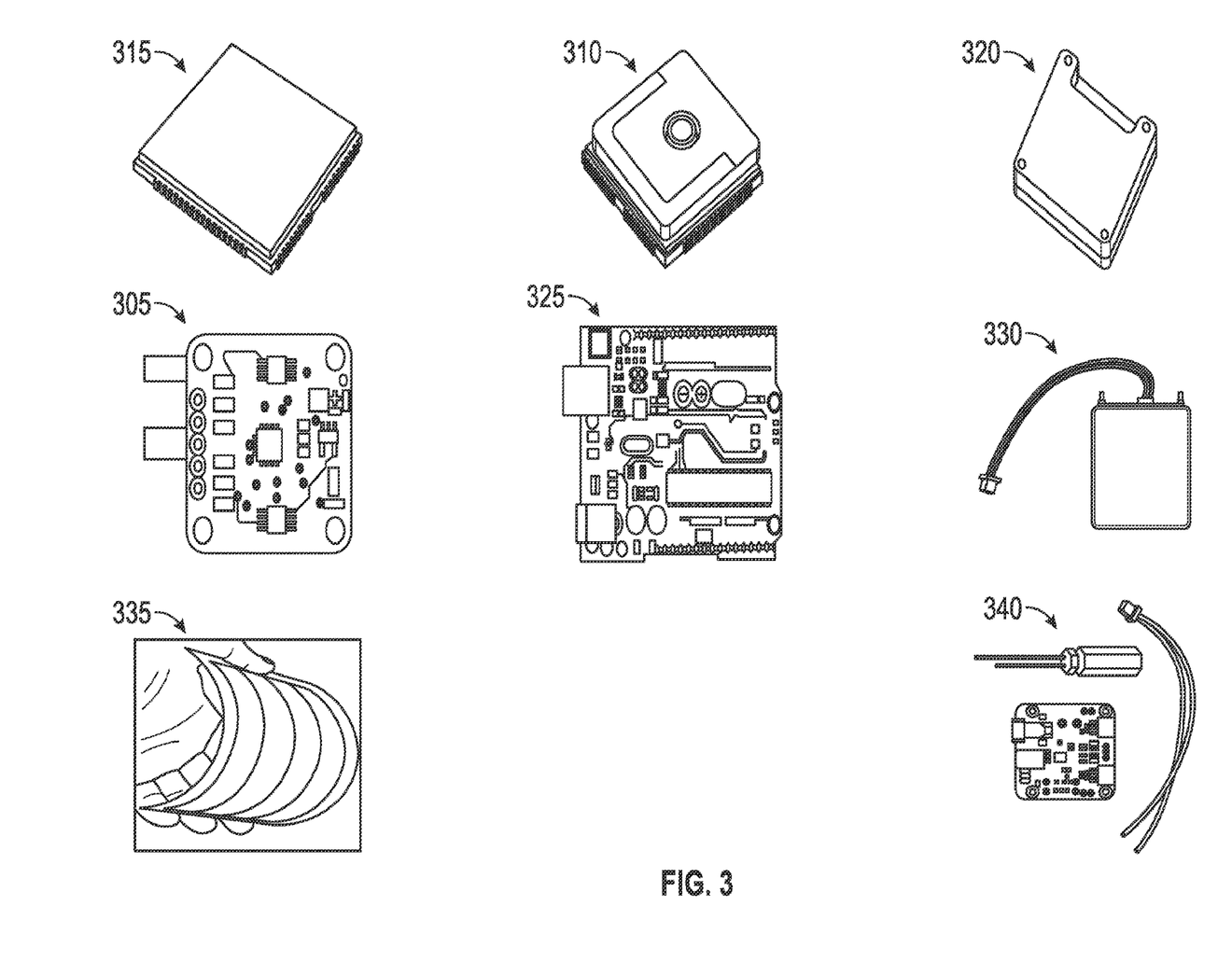
FIG. 3 shows images of potential components of the tracking device shown in FIG. 2.

In embodiments of the present invention the tracking device can be grouped into two versions, a version with satellite communication (225) and a version without satellite communication. A device without satellite communication can communicate with the system via GSM mobile phone networks, but cannot communicate in areas where a GSM mobile phone network is not available. The GSM communications (215) can be for instance a Quectel Quad-band GSM/GPRS M10 Microcontroller (315) as pictured in FIG.

3. On the other hand a tracking device with satellite communication (225) can use GSM mobile phone networks (primary mode of communication) and the Iridium satellite phone network (secondary mode of communication). This allows continuous feedback to the tracking system on transit legs with little to no coverage such as vessel or train. Satellite communications (225) can be a variety of different components such as for instance an Iridium 9602 Satellite Modem (320) as seen in FIG. 3. The Iridium 9602 SBD transceiver (320) provides global tracking via the Iridium satellite network.

The accelerometer (205), GPS tracker (210), GSM communications (215), and satellite communications (225) may be operably connected to a mainboard (220). The mainboard (220) can allow processing of information from the GPS tracker (210) concerning the location of the tracking device (160) and forwarding to the tracking system of said information through the appropriate communications link, e.g. GSM (215) or satellite (220). The mainboard (220) can detect the presence or absence of a GSM signal and thereby can control whether the tracking device forwards location information (e.g. from the GPS tracker (210)) to the system via GSM (215) or satellite communication (225). In various instances the mainboard (220) may encrypt or otherwise protect the tracking information transmitted to prevent interference thereto. The mainboard (220) may be associated with an identifying ID that allows the system to identify the tracking device. In various instances, the mainboard (220) may be partially integrated with each of the various components of the tracking device (160) or may comprise a separate component. In various embodiments the mainboard (220) may take many forms, for example, an Arduino UNO Rev3 (325) as shown in FIG. 3.

Power for the mainboard (220), accelerometer (205), GPS tracker (210), GSM communications (215) and satellite communications (225) and/or other components of the tracking device can flow directly from the power supply (230) to the individual components or via the mainboard (220). In various instances the power supply (230) may be configured to send to the tracking system via the mainboard (220) and communications indications of remaining power. In various instances power will be continuous or it may be regulated by a switch or other mechanism. The power supply (230) can take on a variety of different forms, such as a battery, depending on the design of the tracking device (160). In an embodiment the power supply (230) is a Lithium Ion Polymer Battery—3.7 v 1200 mAh (330) as shown in FIG. 3. In an additional embodiment the power supply (230) includes a battery as well as a solar panel to recharge the battery during daylight hours. As seen in FIG. 3 the solar panel may be a Flexible 6V 1W Solar Panel (335) with the connection to the battery facilitated by, for example, USB/DC/Solar Lithium Ion/Polymer charger—v2 (340).

Depending on application needs, the tracking device (160) may further include additional sensors such as temperature (235), vibration (240) and seal breakage (245), all optionally connected to the mainboard (220), communications, and/or power supply (230). A temperature sensor (235) may be configured to measure the temperature outside the device (160) or inside the device (160). Vibration information can be used by the device and/or tracking system to determine cargo movement and integrity. The seal breakage sensor (245) can be connected to the bolt seal or other type of seal. In various instances the seal sensor can be a conductance based sensor such as a reed switch. A reed switch can be attached to both ends of bolt locking mechanism. When the bolt locking mechanism is locked, the circuit of the reed switch is closed and when unlocked the circuit can be opened.

The housing (250) of the tracking device (160) may be specially tailored to a unique transit application. In some instances, the tracking device may be configured to lock within existing plastic, metal, cable, or padlock seals. Alternatively, the housing (250) may be designed to lock within existing bolt seals.

The tracking system may include plastic, metal, cable, or padlock seals. These seals may be configured to pass through the aperture of the tracking device as well as the central hole of the container door overlapping flanges. These seals may include numbering unique to the load and/or customer and be configured to blush if tampered with. In some instances these seal may include a ball locking mechanism that is difficult/impossible to reseal once broken. Examples of such seals include S-13677, H-541, and H-1346 from Uline™.

Figure 4:
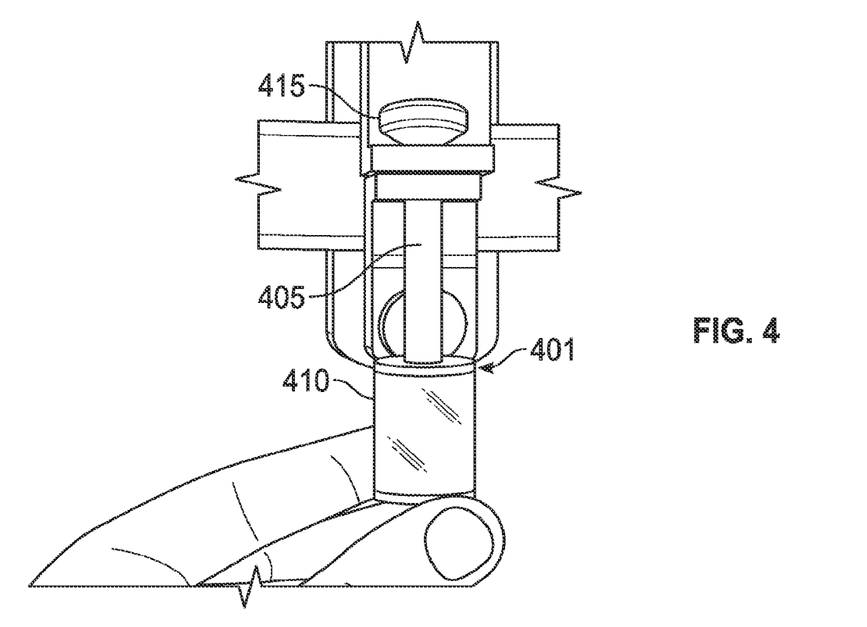
FIG. 4 shows a bolt seal.

Further embodiments of the tracking system may include a bolt seal. Bolt seals can come in a variety of forms. A commercially available bolt seal (401) can be seen in FIG. 4. Depending upon the shipping company a different bolt seal (401) may be used. The bolt seal may include numbering unique to the load and/or customer and be configured to blush if tampered with. Bolt seals can comprise a bolt (405) with a head (415) and a locking mechanism (410). The bolt seal (401) may lock the container (135) and the bill of lading (190) therein preventing access thereto without breaking of the bolt seal (401).

As seen in FIGS. 5, 6, 7, and 8, the housing may include a connector, a support member and a main body. In various embodiments, the tracking device housing may be formed from plastic (e.g. PVC), metal, or other suitable materials. The tracking device housing may include a connector that is adjustable for receiving different types of seals. The connector may be designed to attach to the seal (401) via an aperture so that the tracking device (160) cannot be removed from the seal (401) without breaking the seal. The aperture can be large enough for this purpose (401) yet small enough to derive stability for the positioning of the tracking device (160) from the seal (e.g. to limit swaying and other movement of the tracking device (160) that may damage device integrity). In various embodiments the connector (510) and connector aperture (515) can be dimensioned to fit on a bolt seal bolt (405) between the head (415) and the locking mechanism (410). In various examples a seal sensor may be tied to the aperture and extend to the connector exterior. The connector (510) may have a width of 1 inch and a thickness of 0.13 inches while the aperture (515) of the connector (510) may be 0.38 inches.

Figure 5:
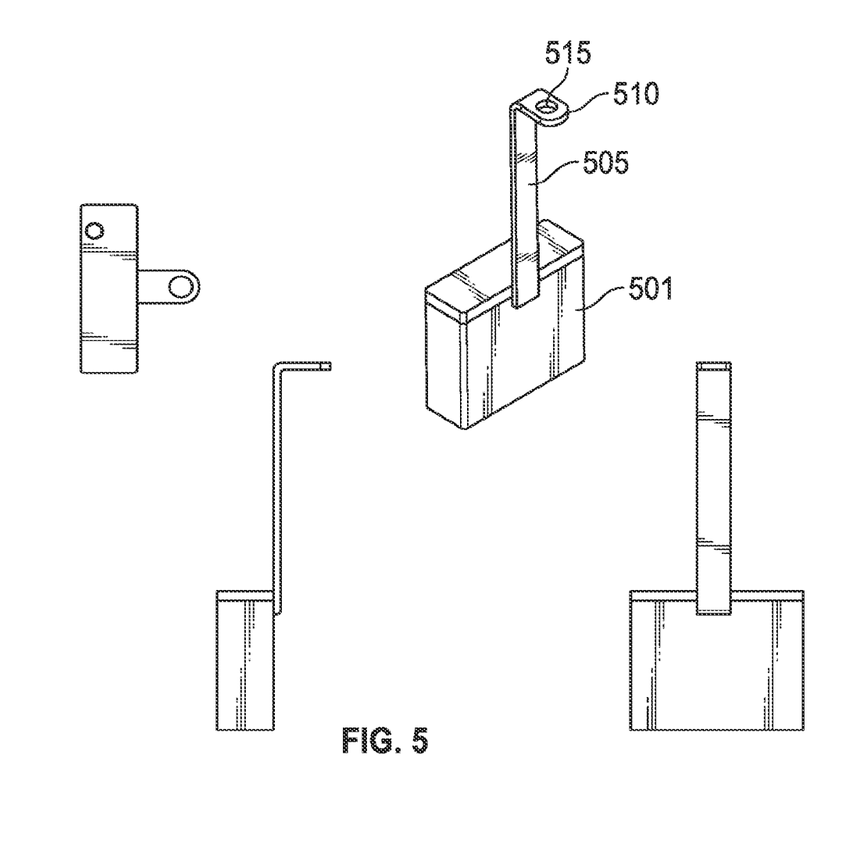
FIG. 5 shows a top, front, right, and isometric view of a housing of a tracking device, according to an exemplary embodiment of the present invention.
Figure 6:
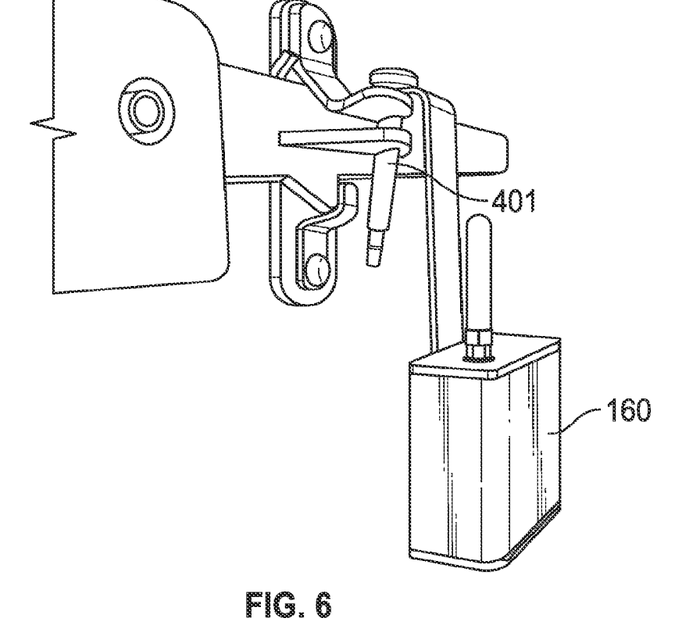
FIG. 6 shows a side view picture of a tracking device without a secured seal, accordingly to an exemplary embodiment of the present invention.
Figure 7:
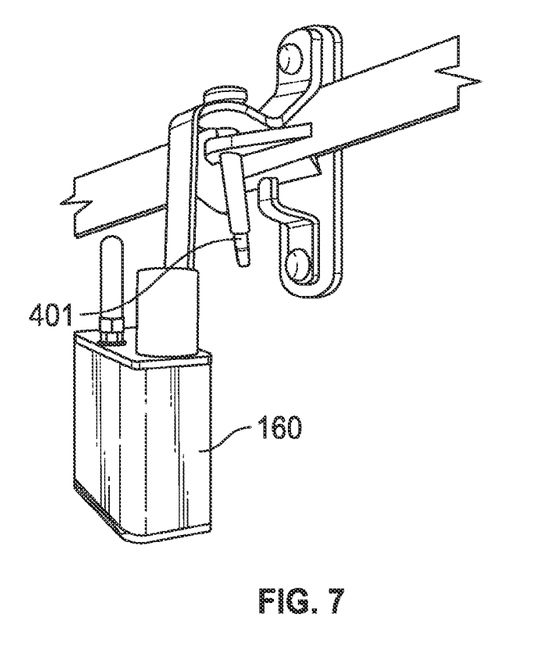
FIG. 7 shows a side view picture of the tracking device shown in FIG. 6.
Figure 8:
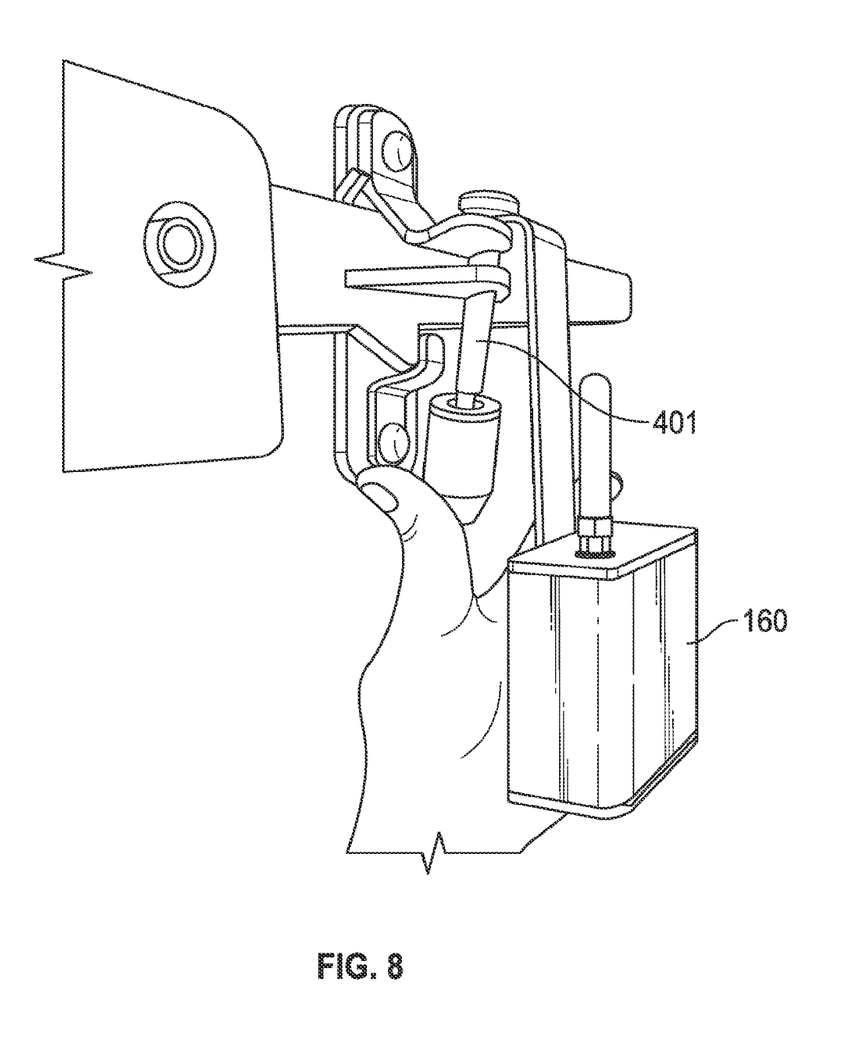
FIG. 8 shows a side view picture of the tracking device shown in FIG. 6 with the seal being secured.

The connector may be conjoined with a support member. The support member can link the connector to the housing main body. The length and geometry of the support member may vary, for example appearing arm-like and extending from a main body as seen in FIG. 5. In various embodiments the tightness of the seal connector connection and the support member's rigidity may act to limit device movement in transit. For example, as seen in FIG. 5, the support member can be linked to a connector sandwiched within the bolt seal with the integrity of the bolt seal connection and rigidity of the support member acting to substantially limit swaying and thereby protecting the tracking device integrity. The connector (505) in some instances may have a thickness of 0.13 inches and a total height of 4.5 inches including 0.5 inches of overlap with the main body (501).

The housing main body may house the mainboard and other important circuitry of the tracking device. The main body housing may take a variety of forms depending on the included circuitry and intended application. In instances the height of the housing (250) may be 6.5 inches, the main body (501) consisting of 2.5 inches and the connector (505) consisting of 4 inches. The main body (501) may have a width of 1 inch and a length of 3 inches. The tracking device may be placed on a container and continuously interact with a tracking system. The tracking system receives information from the tracking device such as latitude, longitude, acceleration, and battery life and makes said information usable to an administrator. The tracking system may include a computer (125) running software operatively connected to the tracking device (160), a user interface (185) and optionally, warehouse terminals.

The computer (125) of the tracking system may encompass any suitable processing device connected to the tracking device. The computer may be physical or web based (e.g. Amazon Web Services). Indeed the computer (125) may be adapted to execute any operating system including Linux™, UNIX™, Windows™, or any other suitable operating system. In some embodiments the computer (125) is a commercially available server, e.g. an IBM System x M5 Tower servers. The computer (125) may be implemented by a processor running software connected to memory and storage. Processor executes instructions, thereby communicating data from a tracking device displaying information related to the tracking, and/or manipulating data. Although described as a single processor, multiple processors may be used according to particular needs. References to processor are meant to include multiple processors where applicable. Memory and storage may include any memory or database module and may take the form of volatile or non-volatile memory including, without limitation, magnetic media, optical media, random access memory (RAM), read-only memory (ROM), removable media, or any other suitable local or remote memory component. The connection of the tracking system computer to the tracking device and/or terminals may be via the internet, internet subnetworks, such as a VPN, or via proprietary network. This connection can be hardwired to the processor or computer system, for example via cat 5 into a network card, or it can be wireless, for example GSM, satellite, or WiFi.

The terminals of the tracking system may comprise an additional desktop computer, iPad, or other network device that is capable of interacting with the tracking system computer. The terminals can be used to activate tracking by the tracking device by warehouse personnel. In other embodiments the tracking system may continuously track the tracking device.

Figure 9:
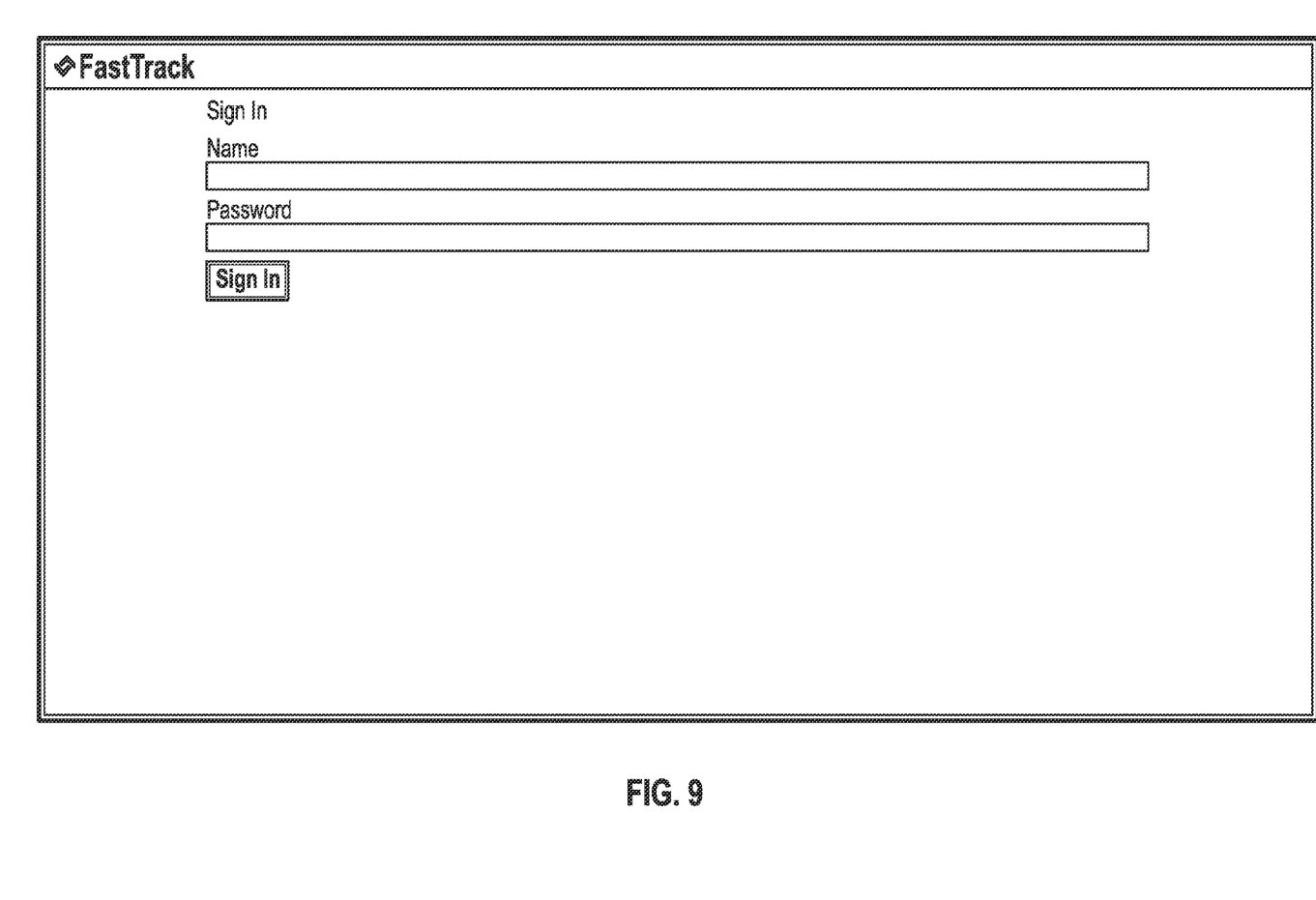
FIG. 9 is a controlled access screen of the tracking system, according to an exemplary embodiment of the present invention.
Figure 10:
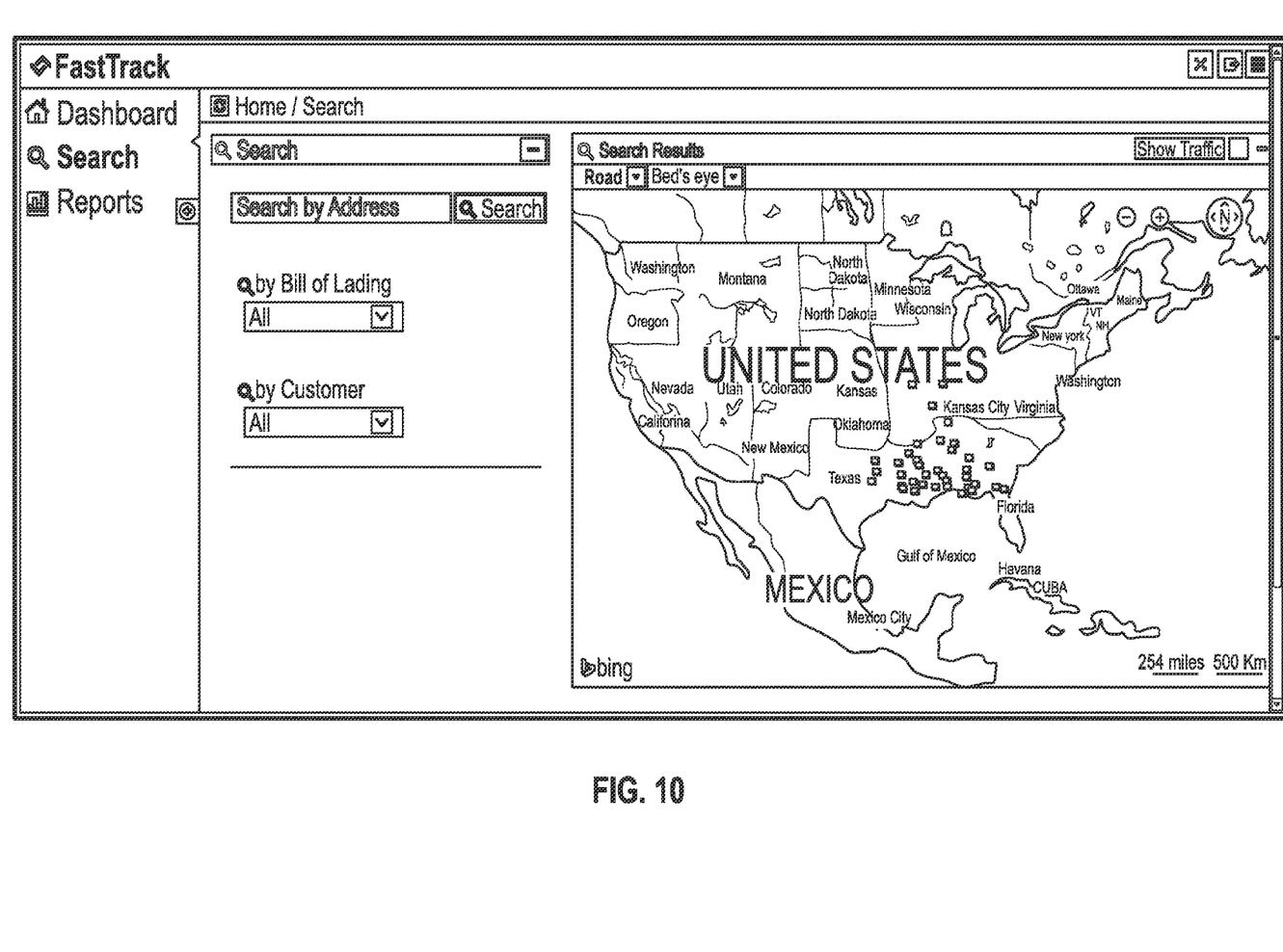
FIG. 10 is a dashboard screen of the tracking system, according to an exemplary embodiment of the present invention.
Figure 11:
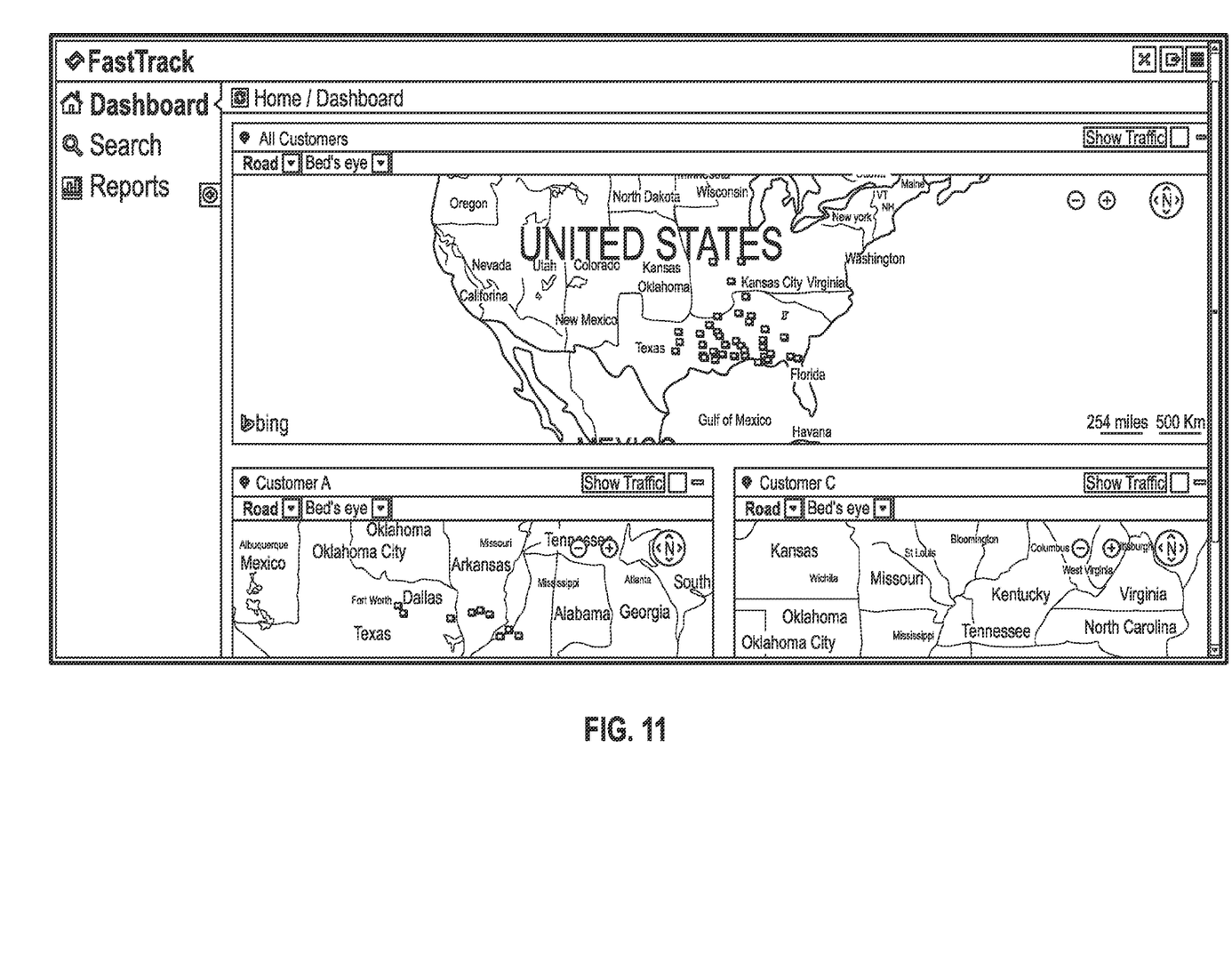
FIG. 11 is a dashboard screen of the tracking system, according to an exemplary embodiment of the present invention.

The software of the tracking system runs on the tracking system computer (125) and can include a web application. In various implementations the software may have controlled access, such as a login screen restricting administrator access as seen in FIG. 9. The software can be displayed on a user interface (185). A user interface (185) may be a monitor connected to the computer, or it may be a more remote interacting platform such as an iPad or android tablet device. In various instances the software may include a dashboard that displays maps as seen in FIGS. 10 and 11. A map displayed can be limited to various criterion such as customer or load type, or the map can display the location of all customer shipments. In various instances the software may allow multiple and/or individual maps to be displayed and certain maps to be minimized, maximized and/or rearranged. In the software the shipments can be represented on the map(s) as truck icons. The truck icons in various instances may be colored green, red, yellow or other colors to indicate shipment status (e.g., green=on schedule, yellow=behind schedule, red=late). The tracking system may establish shipment status based on estimated time of arrival ("ETA") at the destination. On land, the ETA can be derived from current shipment location, the roads (and corresponding speed limits) that must be traversed to reach the destination, and the traffic conditions on said roads. At sea, ETA can be derived from current shipment location, distance to shipment destination, and the speed of the shipment. The software may include an interactive function for the truck icons. Clicking a truck icon may result in the display of a pop-up box, which displays shipment details. The map in various embodiments may be viewed in road view or satellite view. Also, the administrator can overlay traffic data on map by click the "Show Traffic" button.

Figure 12:
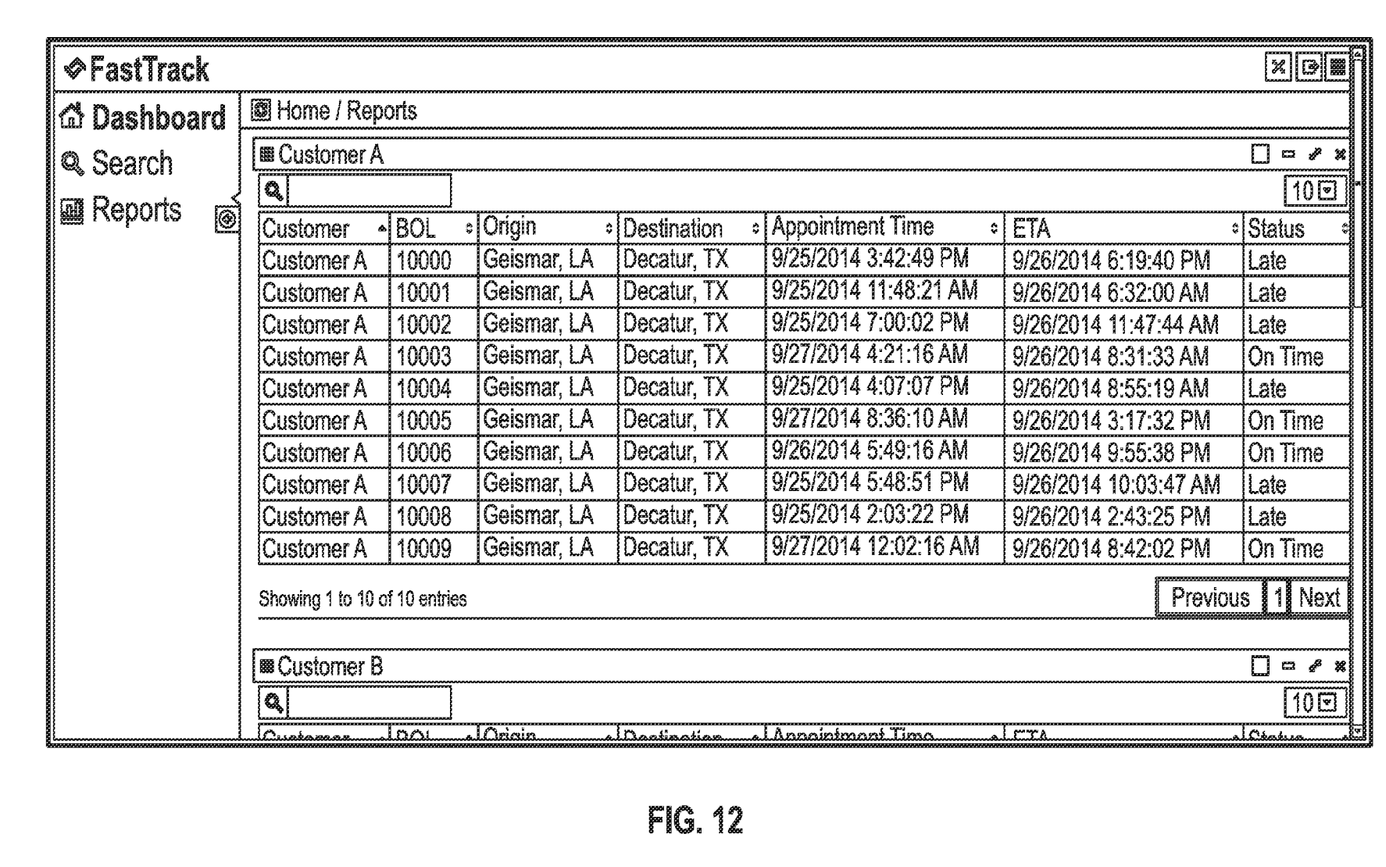
FIG. 12 is a search screen with textual reporting of the tracking system, according to an exemplary embodiment of the present invention.
Figure 13:
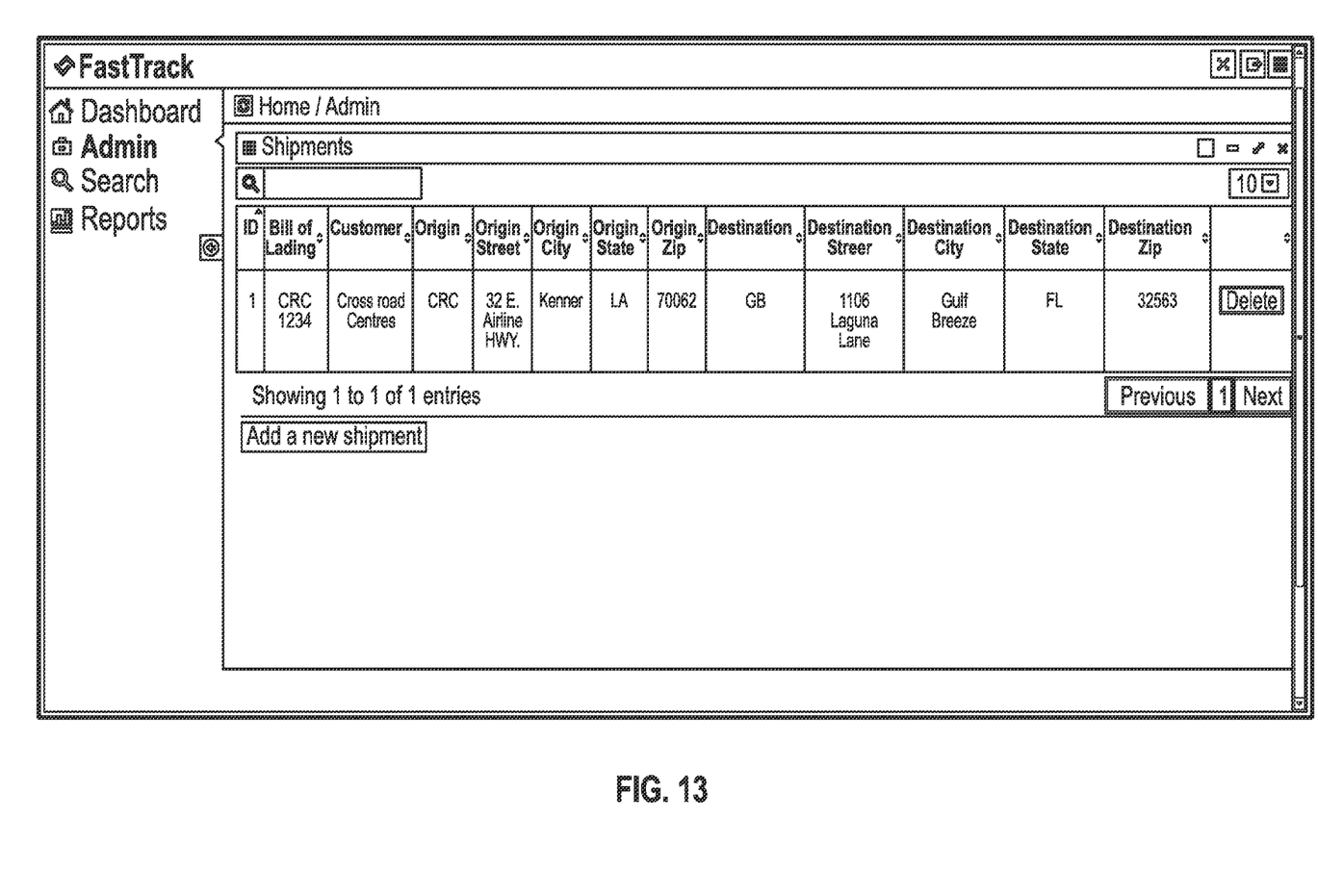
FIG. 13 is an administration screen of the tracking system, according to an exemplary embodiment of the present invention.

The tracking system software may further include a search function with textual reporting as seen in FIG. 12. Shipment status may be searched for by criterion including, for example, destination address, bill of lading, product, carrier, or customer. The search results may display both active and historical loads. The historical data may allow a user to analyze shipment trends by carrier, customer, or product. The tracking system software may include an administration screen as seen in FIG. 13 that provides the functionality to create/delete/edit products, create/delete/edit shipments, assign a tracking device to a shipment, create alerts, or create geofence.

In various embodiments the tracking system may be integrated into a transportation management system, located on the same computer or operably connected thereto. The transportation management system may take parameters from tracking system and use them to manage other elements related thereto. For instance when generating a cost estimate for a customer the transportation management system can screen recent and ongoing trajectories along the route used to base travel time, fuel use, and cost. When planning a route for delivery of freight, the transportation system can use the detailed information from the tracking system to see what intersections to avoid further optimizing overall delivery and pick up. The transportation system can also use information related to the evolving position of a load to appropriately schedule a drop off time for the load or schedule a check-in at a remote check-in facility as described in U.S. patent application Ser. No. 14/506,545, filed Oct. 3, 2014, which is incorporated herein by reference in its entirety. Embodiments of the present invention as described herein can be integrated with various embodiments described in U.S. patent application Ser. No. 14/506,545.

While the embodiments are described with reference to various implementations and exploitations, it will be understood that these embodiments are illustrative and that the scope of the inventions is not limited to them. Many variations, modifications, additions, and improvements are possible. Further still, any steps described herein may be carried out in any desired order, and any desired steps may be added or deleted. Support for the present invention, including example embodiments of the present invention, may be found in the attached documents and figures, all of which are expressly incorporated herein in their entirety by reference hereto.

What is claimed is:

1. A system, comprising:
   a removable tracking device including a vibration sensor;
   a container; and a container seal,
wherein the tracking device is integrated with the container seal,
wherein the tracking device is configured to detect a presence or absence of a GSM signal and to configure a wireless communication channel to be a GSM or satellite communication channel based on the detected presence or absence of the GSM signal,
wherein the tracking device is configured to transmit a location of the container continuously via the wireless communication channel,
wherein the tracking device is configured to measure an acceleration and the location of the container and send the acceleration and the location of the container to a remote computer, and
wherein the vibration sensor is configured to determine vibration data and the tracking device is configured to determine cargo movement and integrity based on the vibration data.

2. The system of claim 1, further comprising a bill of lading, the bill of lading being at least one of stored at a warehouse facility and stored within the tracking device.

3. The system of claim 1, wherein the container seal includes a bolt and a locking member.

4. The system of claim 1, wherein the tracking device includes a rigid support member with a connector at one end of the tracking device that connects the tracking device to the container seal.

5. The system of claim 4, wherein the connector includes an aperture.

6. The system of claim 4, wherein the support member is a rigid elongated member, a first end of the elongated member attached to a housing and the second end of elongated member attached the container such that the container cannot be accessed without breaking the container seal.

7. The system of claim 1, wherein the tracking device includes a sensor that detects temperature.

8. The system of 6, wherein the elongated member and the connector are connected and securely attach the tracking device to the container seal to minimize movement and absorb loading while the container is being transported.

9. The system of claim 1, wherein the connector is a universal connector adaptable for connection to different types of containers.

10. The system of claim 1, wherein the tracking device weighs less than 10 pounds.

11. The system of claim 1, wherein the tracking device includes an accelerometer configured to measure the acceleration of the container, a GPS tracker configured to track the location of the container, a GSM communication device configured to forward the acceleration and location of the container to the remote computer, and a power supply.

12. The system of claim 11, wherein the tracking device includes a sensor connected to the GSM communication that monitors breakage of the container seal.

13. The system of claim 1, wherein the tracking device includes a satellite communication apparatus configured to forward the acceleration and the location of the container to the remote computer if GSM communication is not possible.

14. A system for broker trucking, comprising:
at least one container including a load;
a removable tracking device including a vibration sensor configured to continuously transmit a location of the at least one container via wireless communication, the container being sealed with a container seal;
a computer configured to continuously receive the location of the at least one container from the removable tracking device and store the location; and
a user interface configured to display the location of the at least one container as received by the computer to an administrator,
wherein the tracking device is integrated with the container seal,
wherein the tracking device is configured to measure an acceleration and the location of the container and send the acceleration and the location of the container to a remote computer,
wherein the vibration sensor is configured to determine vibration data and the tracking device is configured to determine cargo movement and integrity based on the vibration data, and
wherein the tracking device is configured to detect a presence or absence of a GSM signal and to transmit information via a GSM or satellite communication channel based on the determination.

15. The system for broker trucking according to claim 14, further comprising a terminal at a warehouse wherein a warehouse personnel inputs into the computer that the at least one container has been loaded and transmits the location of the at least one container.

16. The system for broker trucking according to claim 14, wherein the administrator is located at the user interface and configured to use the location information of the at least one container to update arrival information.

17. The system for broker trucking according to claim 14, wherein the location of the at least one container is transmitted over GSM when available and over the internet to the computer configured to receive the location.

18. The system for broker trucking according to claim 14, wherein the location of the at least one container is transmitted over satellite when available and over and the internet to the computer configured to receive the location.

19. The system for broker trucking according to claim 14, wherein the computer is interconnected with a Transportation Management System.

20. A method of broker trucking, comprising the steps of:
obtaining a tracking device having a vibration sensor for a load;
loading a container, connected to a trailer, with the load;
sealing the container with a container seal;
monitoring the container while the load is in transit using the tracking device;
breaking the container seal;
removing the load from the container; and
returning the tracking device to a depository,
wherein the tracking device is integrated with the container seal,
wherein the tracking device is configured to detect a presence or absence of a GSM signal and to configure a wireless communication channel to be a GSM or satellite communication channel based on the detected presence or absence of the GSM signal
wherein the tracking device is configured to transmit a location of the container continuously via the wireless communication channel,
wherein the tracking device is configured to measure an acceleration and the location of the container and send the acceleration and the location of the container to a remote computer, and wherein the vibration sensor is configured to determine vibration data and the tracking device is configured to determine cargo movement and integrity based on the vibration data.

21. The method of claim 20, further comprising the steps of: inputting into a computer system that the container is ready to depart; and inputting into the computer system that the container has arrived, wherein the inputting activates the tracking device and an inputted arrival deactivates the tracking device.

22. A tracking device for a trailer containing a load, comprising:

a main body, the main body enclosing a GPS tracker configured to track a location of the load, and a vibration sensor, wherein the tracking device is at least one of integrated with and securely attached to the container, wherein tracking device is configured to detect a presence or absence of a GSM signal and to configure a wireless communication channel to be a GSM or satellite communication channel based on the detected presence or absence of the GSM signal wherein the tracking device is configured to transmit the location of the container continuously via the wireless communication channel, wherein the tracking device is configured to measure an acceleration and the location of the container and send the acceleration and the location of the container to a remote computer, and wherein the vibration sensor is configured to determine vibration data and the tracking device is configured to determine cargo movement and integrity based on the vibration data.

23. The tracking device of claim 22, further comprising an accelerometer configured to measure the acceleration of the container, a GSM communication device configured to forward the acceleration and the location of the container to the remote computer, and a power supply.

24. The tracking device of claim 23, further comprising a sensor connected to the GSM communication device that monitors breakage of the container seal.

25. The tracking device of claim 23, further comprising a satellite communication device configured to forward the acceleration and the location of the container to the remote computer if GSM communication is not possible.

* * * * *